United States Patent [19]
Leroy et al.

[11] Patent Number: 5,955,673
[45] Date of Patent: *Sep. 21, 1999

[54] CATHODE SPUTTERING TARGETS SELECTED BY ULTRASONIC INSPECTION FOR THEIR LOW LEVEL OF PARTICLE EMISSION

[75] Inventors: Michel Leroy, Saint-Egreve; Jean Muller, Voiron, both of France

[73] Assignee: Aluminium Pechiney, Courbevoie, France

[ * ] Notice: This patent is subject to a terminal disclaimer.

[21] Appl. No.: 08/631,365

[22] Filed: Apr. 12, 1996

[30] Foreign Application Priority Data

Feb. 13, 1996 [FR] France .................................. 96 01990

[51] Int. Cl.$^6$ .................................................. G01N 29/10
[52] U.S. Cl. ................................ 73/602; 73/628; 73/629; 73/646; 204/298.03; 204/298.13; 204/298.14
[58] Field of Search .............................. 73/602, 620, 627, 73/628, 629, 631, 646; 204/192.13, 192.33, 298.03, 298.12, 298.13

[56] References Cited

U.S. PATENT DOCUMENTS

| | | | |
|---|---|---|---|
| 4,366,713 | 1/1983 | Gilmore et al. | 73/618 |
| 4,741,212 | 5/1988 | Rehwald | 73/600 |
| 5,406,850 | 4/1995 | Bouchard et al. | 73/620 |

OTHER PUBLICATIONS

Patent Abstracts of Japan, vol. 12, No. 443 (P–790), Nov. 22, 1988, JP–A–63–172960, Jul. 16, 1988.
"Using Acoustic Emission to Determine Dynamic Sputter Target Performance" by Anthony B. Cistola, Microelectyronic Manufacturing & Testing, Nov. 1985 pp. 32–33.
"Glow Discharge Optical Spectroscopy for Monitoring Sputter Deposited Film Thickness" by J.E. Greene and F. Sequeda–Osorio, J. Vac. Sci. Technol., vol. 10, No. 6, Nov./Dec. 1973 pp. 1144–1149.
"Attenuation of the Ultrasonic Waves in Metals. I Aluminum" by Hirone et al, Sci. Rpt. Tohoku Univ. First Series, 1955, pp. 455–464.
"Frequency and Grain Size Dependency of Ultrasonic Attenuation in Polycrystalline Materials" by Steven Serabian, British Jour. of NDT, Mar. 1980, pp. 69–77.
"Energy Losses of Sound Waves in Metals Due to Scattering and Diffusion" by WP Mason and HJ McSkimin, Journal of Applied Physics, vol. 19, Oct. 1948 pp. 940–946.

*Primary Examiner*—Hezron Williams
*Assistant Examiner*—Rose M. Miller
*Attorney, Agent, or Firm*—Oblon, Spivak, McClelland, Maier & Neustadt, P.C.

[57] ABSTRACT

A process using ultrasonic inspection for testing the internal soundness of cathode sputtering targets, whose active part is made of aluminum with a very high degree of purity or a very pure aluminum alloy, consisting, after selection of an ultrasound sensor functioning at an operating frequency greater than 5 MHz, preferably between 10 and 50 MHz, and adjusting the appropriate measurement sequence, using a target immersed in a liquid and which has ceratin artificial defects simulating decohesions in the target, taking a count in terms of size and number of the internal decohesions per unit volume and selecting, for the applications requiring a very high degree of etching fineness, the targets with a decohesion density of $\leq 0.1$ decohesion larger than 0.1 mm/cm$^3$ of active metal of the target, and cathode sputtering targets selected according to the process having no more than 0.1 internal decohesion larger than 0.1 mm/cm$^3$ of active metal of the target.

5 Claims, 3 Drawing Sheets

CATHODE SPUTTERING TARGETS SELECTED BY ULTRASONIC INSPECTION FOR THEIR LOW LEVEL OF PARTICLE EMISSION

TECHNICAL DOMAIN

The invention pertains to a process using ultrasonic inspection for testing of the internal soundness of targets or cathodes based on aluminum with a very high degree of purity, which are intended for cathode sputtering on a substrate for manufacturing integrated circuits in particular, as well as to the selected targets coming from this inspection.

STATE OF THE ART

Cathode sputtering is a deposition technique whose principle is described abundantly in the specialized scientific literature. It allows one to deposit practically all types of materials, refractory or nonrefractory, alloyed or not, conductive or dielectric, on all types of substrates which accept being put under vacuum and slight heating. This deposition technique has been applied extensively in electronics for the covering of semiconductor silicon wafers with an aluminum alloy and the manufacturing of integrated circuits. Thus, the manufacturing of integrated circuits with a high level of integration, for example, dynamic memories with a capacity of greater than 4 Mb, requires the deposition of metallic interconnection layers with small thicknesses (approximately 1 $\mu$m), which are then etched to form extremely fine lines (less than 0.5 $\mu$m in width) allowing individual access to each memory position.

One sees that under these conditions, any defect in the metallization layer, whose size is close to the width of an interconnection line, can lead to a redhibitory defect during the etching operation of the integrated circuit and can lead to the rejection of the integrated circuit.

Among these defects in the metallization layers, which are obtained by cathode sputtering under vacuum using a metallic target, one of the most frequent is the tearing of fine particles from the surface of the target and redeposition of these fine solid or liquid or dust particles on the- semiconductor substrate during metallization.

The size of this dust or these particles is generally between a few tenths of a micron to a few microns.

In the case of the earlier generations of integrated circuits, whose etching width was several microns, the majority of the particles thus redepositing on the metallized layer of the substrate did not cause any significant etching defects, and the proportion of metallized substrates rejected because of etching defects for this reason could be tolerated.

In contrast, in the case of the current and future generations of integrated circuits, for example, the dynamic RAM memories of 16 or more Mb, the fineness of etching has been considerably stressed, and the width of the line has been brought to a few tenths of a micron (currently on the order of 0.2–0.5 $\mu$m). Under these conditions, the very fine particles torn from the target and redeposited on the semiconductor substrate have become a major cause for rejection of integrated circuits, and each year, this defect costs the worldwide electronics industry considerable sums of money, greater by several orders of magnitude than the cost of the metallization targets which are used.

It is becoming obvious that eliminating this defect, or at the very least limiting it, is a major stake for the electronics industry and justifies the very extensive research and development efforts on the part of this industry for the purpose of understanding the origin of this defect and remedying it.

These efforts, however, have up to now remained without effect, in spite of the attempts aiming to act on the conditions of preparation of the target, for example, by refinement and homogenization of the sizes of the particles below 0.1 mm according to EP-A-0,466,617 (U.S. Pat. No. 5,160,388). It should also be noted that in this domain, the nondestructive testing methods, particularly the ultrasonic inspection methods for testing, of the regularity of the active metallic layer of the target in comparison with a reference layer with an equivalent average particle size, according to U.S. Pat. No. 5,400,850, do not help explain and a fortiori limit this serious problem.

Various hypotheses have been issued as to the origin of the particles redeposited on the substrate in the course of metallization:

A first hypothesis is a mechanism in two steps:

In a first step, a part of the metal torn atom by atom from the target is deposited on the walls of the sputtering reactor, or on pieces of equipment contained in this reactor, such as the collimating grid located between the sputtering target and the substrate, and forms a fine deposit there.

In a second step, this deposit is torn again from its support, in the form of fine particles, and is thrown onto the semiconductor substrate during metallization.

However, this mechanism, if it exists, can only be completely secondary,.because it does not explain a major observation which is the following:

When one observes a high level of emission and redeposition of particles on several consecutive substrates, it is very often sufficient to change the sputtering target to stop the phenomenon; the emission (and redeposition) of particles is therefore an intrinsic characteristic of the target.

A second hypothesis issued to explain this characteristic effect, connected with an unknown property of the sputtering target, was to suspect the presence of fine inclusions in the metal, such as inclusions of oxides, nitrides, carbides, etc., in the metallic matrix of which the target is composed.

These refractory and electrically nonconductive particles could be electrically charged under the effect of bombardment of the target with argon ions, and could ultimately give rise to the establishment of an electric arc (phenomenon called "arcing"), and then to the melting of the metal surrounding the particle and to its being thrown in the form of multiple micron-sized liquid droplets onto the substrate (phenomenon known as "splashing" or "spattering", or else to the explosion of the refractory particle under the effect of the accumulated electrostatic charge (phenomenon known as dust application or "dusting").

This hypothesis, which calls for the presence of inclusions whose content can vary from target to target, explains certain experimentally observed phenomena well, and in particular the phenomena of local triggering of an electric arc on the target, during use, which is sometimes observed.

Thus, in one publication "Effect of thin film oxide inclusions on aluminum target arcing and particulate" [sic] presented in Minneapolis in October 1995 to the annual congress of the American Vacuum Society, A. Leybovich, R. S. Barley, and J. Poole of Tosoh SMD Inc. indicate that large particles of aluminum oxide ($\phi$>1 mm) coming from local electrochemical oxidation of the surface of the target and distributed parallel to this surface can cause "arcing." However, extensive defects can be detected by conventional ultrasonic inspection between 1 MHz and 3 MHz and are not normally present in the industrial targets after standardized testing providing for elimination of targets in case of a defect level of 0.7 mm.

This phenomenon is therefore not general: it is a "catastrophic" and destructive phenomenon, which is fortunately not very common, and can only explain an often limited fraction of the emissions of submicron particles observed more commonly, except it the metal used to manufacture the target was particularly dirty and in particular had large quantities of large-sized refractory inclusions present initially in the liquid metal or generated during the casting process, for example more than 5 mg of refractory particles with an average size greater than 30 $\mu$m/kg of metal.

Furthermore, this hypothesis does not explain another experimental observation known to experts in the metallization of integrated circuits, which is that the level of particle emission is a function of the alloy constituting the target, aluminum-silicon-copper alloys (for example, Al+1% Si+0.5% Cu) being the most sensitive, followed by the aluminum-silicon alloys (for example, Al+1% Si), and finally the alum-copper alloys with a small copper load (for example, Al+0.5% Cu) being the least sensitive.

No correlation between the chemical composition of the alloy constituting the target and its inclusion content has ever been revealed, and this relationship between the nature of the alloy constituting the target and the level of particle emission has up to now remained a mystery.

The Problem Posed

Supplying the electronics industry with cathode sputtering targets which are certain to have very limited levels of particle emission has not been accomplished regardless of the aluminum-based alloy used.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

OBJECT OF THE INVENTION

Figure 1:
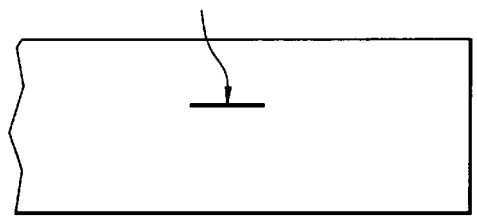
FIGS. 1–5 represent successive phases of damage to the sputtering target during processing.

The process according to the invention for testing the internal soundness of targets made of aluminum or aluminum alloy contributes a solution to this problem and is based on the unexpected observation that there is a correlation between the level of particle emission and the number and size of defects in the residual metal of the target which are present mainly as flat decohesions which can be measured using a suitable ultrasound method, which in particular uses, along with a sensor or probe adjusted to the frequency of operation, a suitable sequence of measurement, that is to say a transmitter which delivers a pulse whose duration is compatible with the frequency of the sensor and a receiver whose sensitivity is maximal in the frequency band used. It should also be noted that the presence of decohesions is sometimes associated with small blisters on the surface of the target.

More precisely, the invention pertains to a process using ultrasound for testing the internal soundness of cathode sputtering targets for the metallization of integrated circuits or electronic circuits, whose active part is made of aluminum with a very high degree of purity or of a very pure aluminum alloy, characterized by the fact that:

After the choice of an ultrasound sensor functioning at a frequency of operation greater than 5 MHz and preferably between 10 and 50 MHz, and adjustment of the appropriate measurement sequence indicating the amplitude of the ultrasound echo of an artificial defect of known size, simulating a decohesion in a target immersed in a liquid, as a function of the position of said defect with respect to the surface of the target:

one determines the size of the decohesions of the targets to be tested, by comparison with the amplitude of the ultrasound echo obtained with the artificial defect in a given volume parameterized by the ultrasonic inspection, one does a count in terms of size and number of the internal decohesions per unit volume of said targets to be tested, one selects, for the applications requiring a very high degree of etching fineness, the targets with a decohesion density of less than or equal to 0.1 decohesion larger than 0.1 mm per cubic centimeter of active metal of the target, and preferably less than 0.01 decohesion per cubic centimeter of said metal.

The invention also pertains to the targets selected according to the process, namely to the cathode sputtering targets, for the metallization of integrated circuits or of electronic circuits, whose active part is made of aluminum with a very high degree of purity or of a very pure aluminum alloy, characterized by the fact that they have at most 0.1 internal decohesion larger than 0.1 mm per cubic centimeter of active metal, and preferably less than 0.01 decohesion per cubic centimeter.

In effect, by attentively observing partially used targets which have given rise to very high levels of particle emission, the applicant curiously observed that several of these targets bad, on the surface eroded by the effect of the arc, minuscule blisters (or bubbles) between 0.1 mm and sometimes up to 1 mm in diameter, certain blisters also being open with eroded edges.

By making sections of these blisters, it was proven that the inside of these blisters was empty and that the base of them was roughly flat and parallel to the initial surface of the target. This base sometimes had a few oxide inclusions or precipitates of alloy elements, but this was not a general phenomenon. In effect, it was more frequent in the case of the alloys with small loads of added elements (for example, Al+0.5% Cu), but it was much less general in the case of the more highly loaded alloys (for example, Al+1% Si+0.5% Cu).

By conducting a test with high-frequency ultrasound at more than 5 MHz on the residual metal of these targets, the presence in this metal of flat decohesions parallel to the base surface of the target was detected. The apparent diameter of these decohesions, as judged in reference to the artificial defect in this case of a flat-bottomed hole 0.1 mm in diameter, was between approximately 0.04 and 0.4 mm. The abundance of these defects was variable but very often exceeded a level of one defect, greater than 0.1 defect with a diameter greater than 0.1 mm, per cubic centimeter of examined metal.

This surprising observation of a correlation between the level of particle emissions, the presence in the residual metal of the target of flat decohesions with dimensions between 0.04 and 0.4 mm, and the presence, on the surface of the used target, of small blisters with a diameter greater than 0.1 mm, constitutes the basis of the invention.

Simply as an attempt at an explanation, it is possible to think that the mechanism leading to the abundant emission of solid or liquid particles of submicron or micron size by a defective target in the course of use could be the following, in reference to FIGS. 1–5 representing successive phases of damage to the target.

The crude casting product from which the defective target originally comes has small decohesions such as microporosities, microcavities, or else refractory inclusions.

During the transformation into target blanks, by forging, pressing, and/or rolling, these arbitrarily shaped decohesions are crushed and flattened parallel to the surface of the blank.

During transformation heat treatments, the hydrogen dissolved in atomic form in the metal and in a state of supersaturation diffuses toward these decohesions and is released there in the form of a molecular gas (whose pressure can reach several atmospheres).

At the time of its positioning in the cathode sputtering apparatus, the defective target therefore has flat decohesions parallel to the surface of the target and filled with molecular hydrogen, according to FIG. 1; these decohesions may contain locally high concentrations of inclusions or precipitates.

Figure 2:
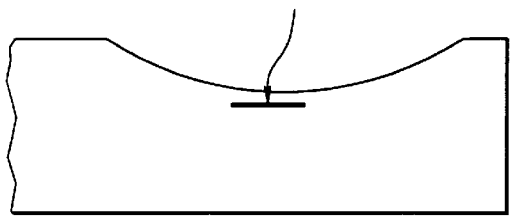

During cathode sputtering, the free surface of the target is progressively eroded until the flat decohesion Inside the target is no longer separated from this surface except by a fine membrane of metal, according to FIG. 2.

Figure 3:
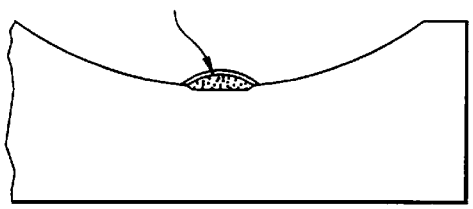

Under the effect of the pressure difference existing between the hydrogen contained in the decohesion and the vacuum predominating in the cathode sputtering chamber, this fine membrane rises and during sputtering gives rise to a blister or protrusion consisting of a fine membrane of metal separated from the metal mass constituting the rest of the target, according to FIG. 3.

Figure 4:
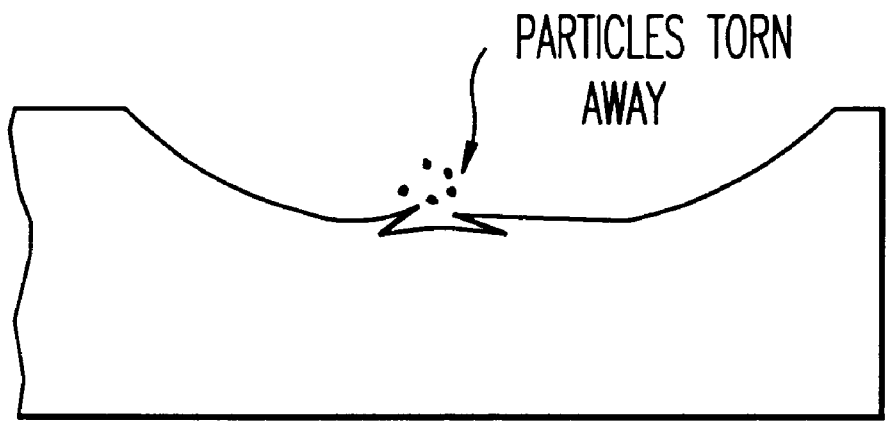

It is then possible to think that this membrane, separated from it massive support, is torn in small solid or liquid fragments during the rest of the cathode sputtering and that these membrane fragments torn from the target redeposit on the substrate in the course of metallization, according to FIG. 4.

Figure 5:
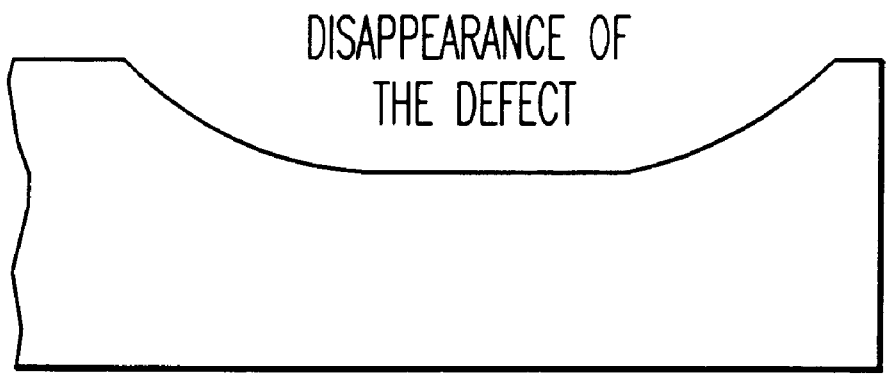

Finally, with the cathode sputtering continuing, the erosion of the surface of the target causes the progressive disappearance of the membrane, according to FIG. 5, and therefore the detect at the origin of the emission of particles.

Figure 6:
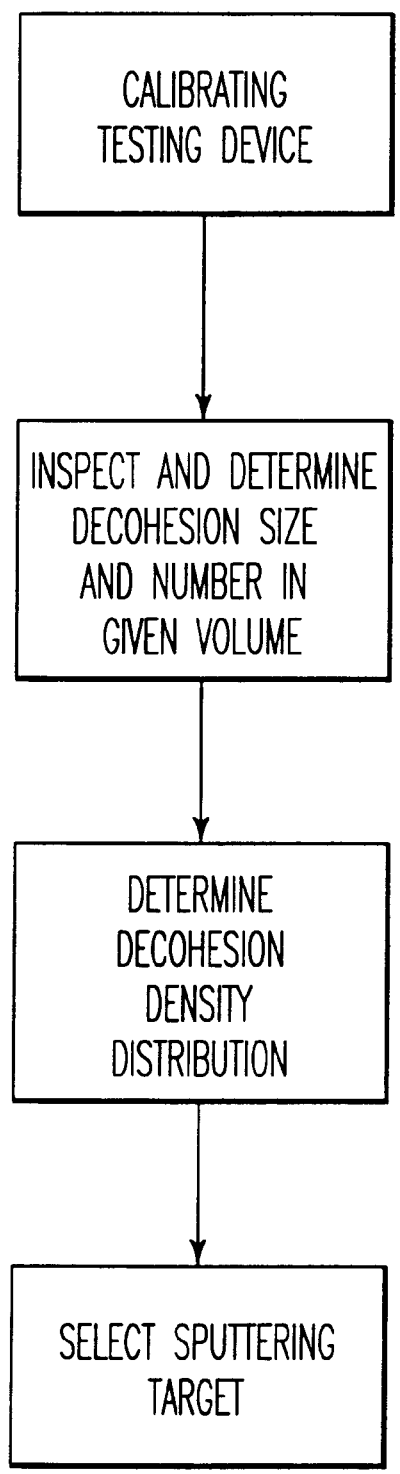
FIG. 6 provides a flow diagram of the process of the present invention.

FIG. 6 provides a flow diagram of the process of the present invention.

Several observations support this mechanism proposal:

On the one hand, one very often observes that the deposit of particles on the semiconductor substrate appears suddenly, affects several consecutive substrates, and then disappears.

This could correspond to the time necessary for the membrane, initially a few tens of microns thick, to be completely eroded and for the defect to have therefore disappeared.

On the other hand, one observes that the alloys most sensitive to the particle emission phenomenon are also those whose solidification interval (that is to say the difference between the temperature at the beginning of solidification and the temperature at the end of solidification) is the greatest: they are also therefore the alloys which are most sensitive to the formation of microporosities or microcavities from contraction at the end of solidification, and with all other conditions equal otherwise (dissolved gas content or inclusion content).

Moreover, on defective targets which have given rise to a high level of particle emission, no blister of very small size, less than 0.1 mm in diameter, was detected, whereas there are numerous flat defects less than 0.1 mm in the residual metal of the target.

This could perhaps be explained in the following way:

For a blister to be able to form, under the effect of the internal pressure of the hydrogen contained in the flat decohesion, it is necessary for the thickness of the metal membrane, separating the decohesion from the surface of the target in the course of erosion, to fall below a critical value which is proportional to the diameter of the decohesion and depends also on the internal hydrogen pressure and on the mechanical strength of the membrane, which is a function of the alloy and the temperature.

For decohesions of very small size (less than 0.1 mm), this critical thickness is very small (less than 10 $\mu$m, as an order of magnitude).

Under these conditions and taking into account the heating of the surface of the target under the effect of the ionic bombardment, the hydrogen present in the decohesion has the time to diffuse through the metal, toward the vacuum of the sputtering chamber, before the residual critical thickness allowing for the formation of a blister is reached.

The decohesion thus being emptied, by diffusion of the hydrogen contained by it through the residual membrane, a blister can no longer form, because the moving force causing its formation (the internal hydrogen pressure) disappears.

This potential explanation based on observation implies as a consequence that only the decohesions with a size greater than the critical size, on the order of 0.1 mm for a metal with an ordinary hydrogen content, that is to say less than 0.20 ppm and preferably less than 0.10 ppm, can give rise to the formation of blisters in the course of operation, and therefore promote the emission of particles which are then redeposited on the semiconductor substrates.

The expert in the field will understand that the order of magnitude of the critical size of the defects giving rise to a blister and then emission of particles can vary as a function of the alloy (mechanical strength of the residual membrane), of the conditions of deposition (surface temperature of the target, speed of erosion of the surface by ion bombardment), etc., and that it is therefore an order of magnitude which applies to the most current alloys and modes of deposition. In certain cases, decohesions between 0.03 and 0.1 mm could also give rise to emission of solid or liquid particles.

As for the implementation of the invention, it will be better understood from the detailed description given below.

DETAILED DESCRIPTION

The process according to the invention is applied to an aluminum alloy containing 1% silicon and 0.5% copper for a target, but it is obviously not limited to this aluminum alloy alone.

Preparation of the Targets

From 13 different casting operations of the same Al+1% Si+0.5% Cu alloy, the applicant removed a section of the crude billet, with a unit length of 600 mm and a crude diameter of 137 mm. The hydrogen content of these cast products was systematically less than 0.20 ppm and generally less than 0.10 ppm as measured with an Alscan® brand apparatus, based on liquid metal in the casting, and confirmed by measurement using a Stroehlein® brand apparatus for extraction of the gas by melting under a vacuum, based on solid samples removed from slices of billets adjacent to the sampled section.

Using these slices adjacent to the 600-mm-long pieces, a test was also conducted for measuring the inclusion content, consisting of dissolving the aluminum alloy matrix and collecting by filtration the insoluble metallic inclusions (filtering threshold≧2 μm), which after drying, are weighed and then counted and measured by scanning microscopy.

The 13 sections of billets were, in a first step, peeled on a lathe in order to eliminate the surface casting skin, and their diameter was brought to 130 mm.

Then, these sections of billets thus peeled were subjected to a conventional ultrasonic inspection at a frequency of 5 MHz, so as to only use the sections with no echo greater than that of an artificial defect represented by a flat bottom [hole] with a diameter of 0.7 mm, according to the French standard AIR No. 9051, which is the most severe standard existing for this type of crude casting product. This led to the rejection of one section.

The sensitivity of this test adjusted to this level of frequency by the choice of an ultrasound sensor and a conventional measurement sequence allows one to detect equivalent defects between 0.3 and 0.8 mm. One will preferably use the standard AIR 9051 in its variant called the helical test, which allows one to inspect 100% of the volume of the billet because the sensor is given a translational movement at right angles with the billet which is itself given a rotational movement, whereas the basic test according to the standard inspects only the surfaces and the three generatrices of the billet.

This led to the rejection of one section which furthermore allowed one to observe that the inclusion content measured on one of the slices adjacent to this section exceeded 10 mg of inclusions with a size greater than 2 μm/kg of metal, whereas this content remained lower than 5 mg of inclusions with a size greater than 2 μm/kg of metal on all the slices adjacent to the 12 sections which satisfied the requirements of this first ultrasound test.

The 12 sections thus selected were then transformed into target blanks, according to the mode of operation described in EP-A-0,466,617 (U.S. Pat. No. 5,160,388) attributed to the applicant, except that the homogenization treatment was slightly adapted for this alloy in particular:

This homogenization was done in two stages, the first stage corresponding to maintaining [a temperature of] 510° C. for 8 h, so as to put the constituents of the ternary eutectic appearing at the end of solidification back in solution, followed by a second stage consisting of maintaining [a temperature of] 560° C. for another 4 h, in order to perfect the homogeneity of the chemical composition of the product, on the scale of the individual particles. After sectioning each billet approximately 600 mm thick into three pieces 160 mm wide separated by control sections, the rest of the operations was carried out entirely according to the instruction of the aforementioned patent and led to target blanks with a diameter of approximately 330 mm and a thickness of 25 mm, after finishing operations including pressing, crosswise rolling, and a final recrystallization heat treatment, at a rate of three targets per piece with an initial length of 600 mm. One surface of each blank was then machined and polished so as to examine the micrographic structure of the transformed products.

This examination revealed that the products contained fine precipitates of silicon and intermetallic $Al_2Cu$, whose average size was in the range of 5 to 10 μm, and that the grain size of these recrystallized products was less than 0.1 mm and, on average, on the order of 0.07 mm.

Furthermore, the texture of these targets, as revealed by an X-ray examination (pole FIGS. 111 and 200), was very perceptibly isotropic, without preferential orientations of the grains.

All the blanks thus produced therefore corresponded, for all these criteria (size of the precipitates, grain size, texture of orientation of the grains), to all the criteria expected for satisfactory use of the targets for metallization of integrated circuits.

These blanks then underwent final machining, on a lathe to obtain disks with a diameter of 300 mm and a thickness of 20 mm, with a unit weight of approximately 3.8 kg, and a volume close to 1,400 $cm^3$. The ultrasonic inspection conducted manually by moving the sensor parallel to the surface of the target with a sensor/target contact produced by a mineral grease, at a frequency of 5 MHz, allowed one to eliminate the disks with equivalent defects or with the artificial defect consisting of a flat-bottomed hole of 0.7 mm, according to the French standard AIR No. 9051. This standard used preferably for crude casting products can be advantageously replaced by standards more frequently used for transformed products, such as AECMA-Pr EN 2003-8 and Pr EN 2004-2 or else MIL STD 2154 and Pr EN 4050-4.

Six blanks out of 36 were thus rejected in this test.

Selection After High-Frequency Ultrasonic Inspection

Before connecting the remaining disks by welding them to their copper support plate they underwent an additional test using high-frequency ultrasound.

This additional test consisted of immersing each machined disk in a tank of water Then, an ultrasound sensor or probe functioning at a frequency of 15 MHz was moved parallel to the surface of the disk according to an X-Y scanning.

This sensor was previously calibrated with respect to artificial defects consisting of flat-bottomed holes with a diameter of 0.1 mm, located at depths of 6 mm, 12 mm and 18 mm under the surface of an identical alloy with metallurgical characteristics similar to those of the product to be tested. It should be noted on this subject that this standard plate, which itself had an average grain size of 0.07 mm, an isotropic orientation of the grains, and small intermetallic precipitates (on the average less than 10 μm), allows as well for a standardization of the sizes of defects on other aluminum alloys with small loads with identical morphological characteristics.

This made it possible to plot the standardization curve giving the measurement of the amplitude of the echo corresponding to an equivalent flat-bottomed hole.

For each disk, the number of echoes exceeding the noise level and the amplitude of the associated signal were counted, in the maximum active volume, as well as the number of echoes exceeding the amplitude corresponding to the artificial 0.1 mm defect, that is to say, a volume of approximately 1000 $cm^3$ corresponding to an active surface with a diameter of 280 mm, over a depth of 18 mm below the surface.

The disks thus tested were separated into five categories:

Category 1 Disks with more than 1000 echoes>0.1 mm per disk (more than 1 echo/$cm^3$)

Category 2 Disks with 100 to 1000 echoes>0.1 mm per disk (0.1~1 echo/$cm^3$).

Category 3 Disks with 10 to 100 echoes>0.1 mm per disk (0.01–0.1 echo/$cm^3$).

Category 4 Disks with fewer than 10 echoes>0.1 mm per disk (less than 0.01 echo/$cm^3$).

Category 5 Disks having only indications between 0.03 and 0.1 mm of which none is greater than 0.1 mm per disk.

The disks of these five categories, all in accordance with the selection criteria existing for sputtering targets, concerning the grain size, the orientation texture, the size of the precipitates, and the absence of defects larger than 0.7 mm, were then connected by welding them to their copper supports.

One then obtained:

3 targets of category 1 (more than 1 echo/cm$^3$ of active metal)

10 targets of category 2 (0.1–1 echo/cm$^3$ of active metal)

12 targets of category 3 (0.01–0.1 echo/cm$^3$ of active metal)

5 targets of category 4 or 5 (less than 0.01 echo/cm$^3$ of active metal).

These targets were then used by a manufacturer of integrated circuits for the metallization of 8-in diameter substrates for manufacturing dynamic RAM memories of 16 Mb.

Results of the Comparative Metallization Tests

Out of the three targets of category 1, two had to be stopped very quickly, with extremely frequent appearances of microarcs and the abundant deposition of particles on the substrates, leading to 100% rejection of these substrates., The third target was used until the normal end of its lifetime, but with mediocre results: more than 20% of the substrates metallized with this target had to be rejected because of the excessive presence of particles larger than 0.5 μm.

Out of the ten targets of category 2, two had to be stopped before the normal end of their lifetime, because of the very frequent appearances of microarcs and abundant deposits of particles on the substrates. The other eight gave mediocre results, on the average more than 10% of the substrates rejected after metallization.

With regard to the twelve targets of category 3, none had to be stopped during use, and on the average less than 5% of the metallized substrates had to be rejected because of the abundant presence of particles.

Finally, with regard to the five targets of categories 4 and 5, none gave rise to problems, and the proportion of metallized substrates which had to be rejected because of the abundant presence of particles was on the average less than 2%.

It was possible to note also that the measurements of inclusion content made on slices adjacent to the pieces from which the targets of categories 3, 4, and 5 came showed a weight content of less than 5 mg of inclusions per kilogram of metal for all the targets. On the other hand, several of these targets, of the preceding categories 1 and 2, obtained also from such pieces, and therefore with similar inclusion contents, provided confirmation that a low inclusion content was without a doubt a necessity but in no case a sufficient condition for obtaining a low level of redeposition of the particles.

Other Application Examples

A) Aluminum alloy containing 1% silicon

Using existing lots of cathode sputtering targets coming from different casting operations and produced out of the same aluminum alloy with a very high degree of purity, greater than 99.999%, containing addition of 1 wt % silicon, one performed a high-frequency (15 MHz) ultrasonic inspection in immersion, and one selected:

on the one hand, a first lot of five targets containing less than 0.1 decohesion with an equivalent size greater than 0.1 mm, per cubic centimeter of metal, and no defect greater than 0.7 mm on the other hand, a second lot of five targets containing more than 2 decohesions with an equivalent size greater than 0.1 mm per cubic centimeter of metal, without any of these defects exceeding an equivalent size greater than 0.7 mm.

The targets thus selected as a function of the density of defects between 0.1 and 0.7 mm were used on an experimental basis, alternately, in the same cathode sputtering machine, for metallizing a series of semiconductor substrates with a diameter of 6 in (approximately 150 mm), with the thickness of the deposited aluminum being 1 μm. Each target was then used to metallize several tens of consecutive substrates.

These substrates were then sorted on the basis of the criteria used for etching integrated circuits of the 16 Mb dynamic RAM memory, with an etching fineness of 0.35 μm.

It was then observed that more than 95% of the substrates metallized from targets with a very low density of decohesions larger than 0.1 mm were judged suitable for this application according to these criteria concerning the presence or absence of deposited particles.

In contrast, more than 20% of the substrates metallized from targets with a high density of decohesions larger than 0.1 mm but smaller than 0.7 mm were judged unacceptable for this application, according to the same criteria.

B) Aluminum Alloys Containing 0.5% Copper

After use in an apparatus for metallization of semiconductor substrates with a high integration density, targets were selected, which were partially used (depth of erosion on the order of 5 mm) made of a binary Al+0.5% Cu alloy, which gave rise to high levels of redeposition of solid or liquid particles on the substrates thus metallized, these high levels of redeposition having led to rejection of more than 10% of these substrates.

These partially used targets, in a first step, were separated from their copper support plates and then remachined dry (with no machining lubricant) with a diamond tool, in order to eliminate their surfaces which were possibly oxidized or contaminated.

These targets thus remachined were then subjected to an ultrasonic inspection, first in a wide frequency band of 10–25 MHz, centered on 15 MHz, and allowing one to detect and count the defects with a diameter greater than or equal to 0.4 times that of a standard flat-bottomed hole with a diameter of 0.1 mm.

It was then observed that all these targets thus remachined, coming from defective targets, contained a defect density greater than 1 defect of equivalent size greater than 0.04 mm per cubic centimeter of metal inspected.

In contrast, for this alloy with a low solidification interval, and curiously, only two targets out of the four targets which contained more than 0.05 defect with an equivalent size greater than 0.1 mm per cubic centimeter of metal inspected resulted.

Each target thus inspected was then diametrically resawed to obtain two semicircular half-targets.

One half-disk per target was then subjected to a dissolution test, for the purpose of dissolving the aluminum alloy matrix and quantifying the initial content of the initial target in terms of insoluble refractory inclusions.

It was thus observed that the defective targets subjected to this test contained more than 5 mg of refractory inclusions per kilogram of alloy.

The other half-disk coming from each target was machined in such a way as to extract from it a solid cylindrical sample for measuring the content of these samples in terms of dissolved or occluded hydrogen, using a Stroehlein® apparatus. It was thus observed that the hydrogen content of the metal coming from the defective targets was greater than 0.12 ppm.

For the sake of comparison, after a sputtering test of limited duration (approximately 25% of their normal lifetime), four metallization targets were removed, which, during this test of significant but limited duration, gave a very low level of rejection due to redeposition of solid or liquid particles (less than 1% rejection).

These partially used targets were subjected to the same examinations as those corresponding to the defective targets.

It was thus observed that these targets of excellent quality systematically had refractory inclusion contents of less than 4 mg/kg of metal and dissolved or occluded hydrogen contents of less than 0.07 ppm.

None of these targets had any internal decohesion larger than 0.1 mm, and less than 0.05 decohesions larger than 0.04 mm/cm³ of metal thus examined; which was considerably lower than that observed using the "defective" targets.

C) Nonalloyed Aluminum with a Purity of 4N to 6N

As a nonlimiting example, out of the existing lots of cathode sputtering targets coming from rolling using a crude casting blank with a rectangular section of aluminum with a purity greater than 99.998%, one selected after 15-MHz ultrasonic inspection:

on the one hand, a first lot of five rectangular targets containing less than 0.01 decohesions with an equivalent size greater than 0.1 mm, per cubic centimeter of metal, and no defect larger than 0.7 mm;

on the other hand, a second lot of five targets containing more than 0.5 decohesions with equivalent size greater than 0.1 mm, per cubic centimeter of metal, with none of these defects exceeding an equivalent size of greater than 0.7 mm.

The targets thus selected as a function of their density of defects with size between 0.1 mm and 0.7 mm were used experimentally, alternating in a cathode sputtering machine, in order to metallize a series of 500 rectangular substrates, intended for the production of liquid-crystal devices with dimensions of approximately 21×28 cm (screens called "14-in"), with a thickness of deposited aluminum of 1 μm. Each target was used to metallize 50 consecutive substrates.

These substrates were then sorted as a function of the criteria ordinarily used for the etching of these rather large screens, in which any local etching defect leads to the rejection of the whole metallized substrate.

It was then observed that more than 95% of the substrates metallized from targets with a very low density of decohesions larger than 0.1 mm were judged suitable for this application according to these criteria concerning the presence or absence of deposited particles.

In contrast, more than 15% of the substrates metallized from targets with a high density of decohesions larger than 0.1 mm, but smaller than 0.7 mm, were judged unacceptable for this application, according to these same criteria.

Value of the Invention

These various application examples demonstrate the great economic value of the invention since, from cathode sputtering targets, for the metallization of integrated circuits or electronic circuits, selected in a suitable manner by a method which does not destroy said targets, it is possible to reduce the level of rejection of the metallized substrates due to redeposition of solid or liquid particles to less than 5%.

We claim:

1. A process for testing internal soundness of a sputtering target for the metallization of integrated circuits or electronic circuits, wherein the sputtering target has an active portion comprising high purity aluminum or aluminum alloy, comprising:

providing a testing device comprising an ultrasound sensor that functions at an operating frequency of greater than 5 MHZ;

calibrating said testing device to indicate an amplitude of an ultrasound echo of an artificial defect of known size that simulates a decohesion in a target immersed in a liquid, as a function of position of said artificial defect with respect to a surface of the target;

inspecting a given volume of the sputtering target to determine the number of decohesions detected in said given volume and the size of said detected decohesions, by comparison with said amplitude of said ultrasound echo of said artificial defect, determining a distribution in size and number of detected decohesions per unit volume of the sputtering target to obtain a density of decohesions having sizes exceeding a given value; and selecting for use the sputtering target if said sputtering target has a density of decohesions larger than 0.1 mm, which is less than or equal to 0.1 decohesion per cubic centimeter of active metal of the sputtering target.

2. The process according to claim 1, wherein the sputtering target selected by the process has a density of decohesions larger than 0.1 mm, which is less than 0.01 decohesions per cubic centimeter of active metal of the sputtering target.

3. The process according to claim 1, wherein the ultrasound sensor has an operating frequency of from 10 to 25 MHZ and the sputtering target selected by the process has no internal decohesions larger than 0.1 mm and a density of decohesions larger than 0.04 mm, which is less than 0.05 decohesions per cubic centimeter of active metal of the sputtering target.

4. The process according to claim 1, wherein the ultrasound sensor has an operating frequency of from 10 to 50 MHZ.

5. The process according to claim 1, wherein the ultrasound sensor has an operating frequency centered on 15 MHz.

* * * * *